(12) United States Patent
Bosco

(10) Patent No.: US 10,143,631 B2
(45) Date of Patent: Dec. 4, 2018

(54) PACIFIER WITH SANITIZING COMPONENT

(71) Applicant: Marie Bosco, Ottawa (CA)

(72) Inventor: Marie Bosco, Ottawa (CA)

( * ) Notice: Subject to any disclaimer, the term of this patent is extended or adjusted under 35 U.S.C. 154(b) by 42 days.

(21) Appl. No.: 14/599,239

(22) Filed: Jan. 16, 2015

(65) Prior Publication Data

US 2016/0206518 A1 Jul. 21, 2016

(51) Int. Cl.
*A61J 17/00* (2006.01)
*A61B 90/70* (2016.01)

(52) U.S. Cl.
CPC .............. *A61J 17/008* (2015.05); *A61B 90/70* (2016.02); *A61J 17/001* (2015.05)

(58) Field of Classification Search
CPC ..... A61B 17/00; A61B 17/001; A61B 17/005; A61B 17/008; A61B 17/02; A61B 90/70; A61B 1/122; A61B 2090/701; A61B 2090/702; A61M 39/16; A61M 39/162; A61L 2/18; A61J 17/00; A61J 17/001; A61J 17/005; A61J 17/008; A61J 17/02; A61J 17/002; A61J 17/003; A61J 17/006; A61J 17/007; A61J 11/008; A61J 11/0085; A61J 11/00; A61J 11/0035; A61J 11/004; A61J 11/0045; A61J 11/005; A61J 11/0055; A61J 11/006; A61J 11/0065; A61J 11/007; A61J 11/0005; A61J 11/0015; A61J 9/08; A61J 9/085; A61J 7/0053
USPC .......................... 606/234–236; 215/11.1–11.6
See application file for complete search history.

(56) References Cited

U.S. PATENT DOCUMENTS

| | | | | |
|---|---|---|---|---|
| 4,329,996 A * | 5/1982 | Copeland | .............. | A61J 17/008 606/234 |
| 4,493,324 A * | 1/1985 | Johnston | ............... | A61J 17/008 606/236 |
| 4,867,159 A * | 9/1989 | Fulton | ..................... | A61J 17/00 606/236 |
| 5,606,871 A * | 3/1997 | Hansen | ................... | A61J 17/00 606/235 |
| 5,964,784 A * | 10/1999 | Wang | ...................... | A61J 17/00 606/234 |
| 2003/0217423 A1 * | 11/2003 | Larsen | ...................... | A61L 2/26 15/104.92 |
| 2005/0065551 A1 * | 3/2005 | Rosuck | ................. | A61J 17/008 606/234 |

(Continued)

*Primary Examiner* — Darwin Erezo
*Assistant Examiner* — Katherine Schwiker
(74) *Attorney, Agent, or Firm* — Mu P.C.

(57) ABSTRACT

A pacifier comprising a guard, having a first surface and an opposing second surface, the second surface having a threaded connector, a nipple attached to and outwardly extending from the first surface of the guard, a detachable cleaning component, having an opening and an interior surface, and a plurality of bristles attached to the interior surface and extending inwardly, where the opening is configured to receive the threaded connector, sealingly connecting the guard and the cleaning component. A method of using the pacifier comprising separating the guard from the cleaning component, inserting the nipple into the cleaning component through the opening, moving the nipple within the cleaning component, such that the bristles contact the nipple, removing the nipple from the cleaning component; and sealing the cleaning component to the guard.

5 Claims, 3 Drawing Sheets

(56) References Cited

U.S. PATENT DOCUMENTS

| | | | | |
|---|---|---|---|---|
| 2006/0226044 | A1* | 10/2006 | Lobl | A61J 17/008 206/438 |
| 2006/0265013 | A1* | 11/2006 | Holley, Jr. | A61J 17/008 606/234 |
| 2007/0012248 | A1* | 1/2007 | Aucoin | B08B 3/00 118/270 |
| 2009/0242000 | A1* | 10/2009 | Jimenez | B08B 3/02 134/135 |
| 2012/0203277 | A1* | 8/2012 | Forestieri | A61J 17/02 606/235 |
| 2013/0089276 | A1* | 4/2013 | Noble | B65D 85/00 383/42 |
| 2013/0197485 | A1* | 8/2013 | Gardner | A61M 39/162 604/533 |
| 2015/0017871 | A1* | 1/2015 | Deane | A45F 5/02 446/227 |
| 2015/0148740 | A1* | 5/2015 | McNac, III | A61J 17/006 604/77 |

* cited by examiner

PACIFIER WITH SANITIZING COMPONENT

FIELD OF INVENTION

This invention relates generally to pacifiers. More specifically, this invention relates to a pacifier with a detachable body that is capable of cleaning the nipple by use of bristles, as well as the method of use.

BACKGROUND

Parents commonly use pacifiers to quiet and soothe crying infants. Because a pacifier is held in an infant's mouth, it is particularly important that the pacifier is clean and germ-free. However, because an infant often allows a pacifier to fall out of its mouth, pacifiers are easily and frequently soiled. Unfortunately, when the infant is away from home or other readily-available sources of running water, it is often difficult for the parent to clean the soiled pacifier. Traditionally, if there is nothing convenient to wash the pacifier off with, the parent or guardian of the child might lick or stick the pacifier in their own mouth to rid the pacifier of any germs or debris collected when it came in contact with the surface on which it was dropped. However, this only replaces or adds to the germs from the ground with the germs from the parent or guardians mouth. Thus, an apparatus which allows a parent to clean a pacifier "on the go" offers great utility.

Some devices have been developed to clean pacifiers; however, these devices are usually separate from the pacifier, requiring the parent to keep both the pacifier and the cleaning device handy. One patent (U.S. Pat. No. 4,329,996) integrates the cleaning device into the pacifier, but lacks both bristles that will facilitate removing germs or debris and a guard to keep a infant from swallowing or choking on the pacifier.

Therefore, there is a need for a safe pacifier with a guard and detachable body capable of cleaning the nipple by use of a cleaning solution and bristles.

SUMMARY OF THE INVENTION

The present invention overcomes these and other deficiencies of the prior art by providing a pacifier comprising a guard, having a first surface and an opposing second surface, the second surface having a threaded connector, a nipple attached to and outwardly extending from the first surface of the guard, a detachable cleaning component, having an opening and an interior surface, and a plurality of bristles attached to the interior surface and extending inwardly, where the opening is configured to receive the threaded connector, sealingly connecting the guard and the cleaning component.

In an embodiment of the invention, the pacifier can have a tether connecting the guard to the cleaning component. In an embodiment, a sanitizing solution can be added to the cleaning component to sanitize the nipple.

In addition, a method of using the pacifier is provided in the present invention that includes separating the guard from the cleaning component, inserting the nipple into the cleaning component through the opening, moving the nipple within the cleaning component, such that the bristles contact the nipple, removing the nipple from the cleaning component; and sealing the cleaning component to the guard.

The foregoing, and other features and advantages of the invention, will be apparent from the following, more particular description of the preferred embodiments of the invention, the accompanying drawings, and the claims.

BRIEF DESCRIPTION OF THE FIGURES

For a more complete understanding of the present invention, the objects and advantages thereof, reference is now made to the ensuing descriptions taken in connection with the accompanying drawings briefly described as follows.

DETAILED DESCRIPTION

Figure 1:
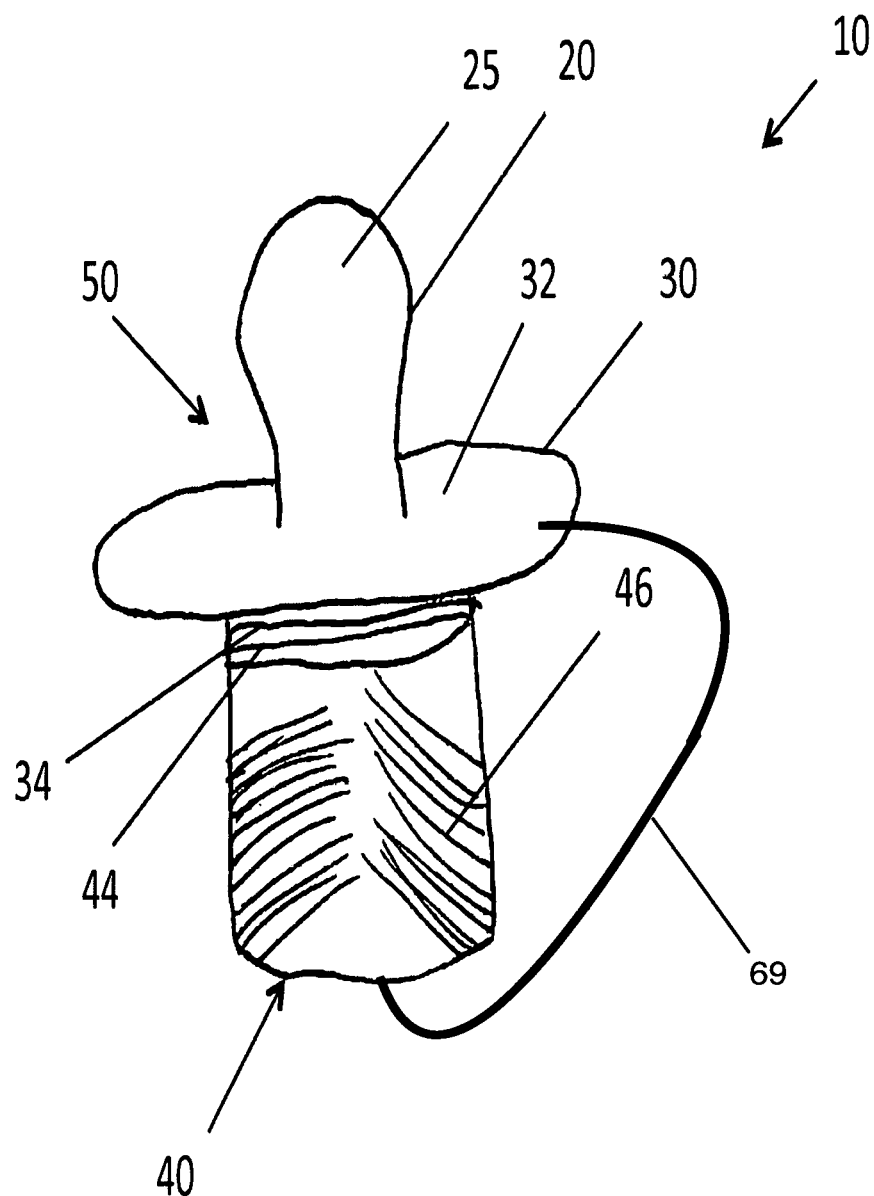
FIG. 1 shows a side elevation view of the pacifier, according to an embodiment of the present invention.

FIG. 1 shows an embodiment of the pacifier 10 comprising a mouthpiece portion 50, which includes a nipple 20 and a guard 30, with a detachable cleaning component 40 attached to the rear of the pacifier. The nipple 20 is elongated in shape and has a bulbous end portion 25 which extends away from guard 30 and which is adapted to be comfortably accepted by the mouth of an infant. Preferably, nipple 20 is of a soft plastic or rubber construction, and is securely joined to the guard 30. Guard 30 is generally flat or curved in specific places to comfortably fit over the infant's lips. Guard 30 may have apertures to prevent suction against the mouth of the infant, and build-up of saliva, and guard 30 prevents entry into the infant's mouth to avoid swallowing or choking Further, guard 30 can be circular in shape or more commonly, oval or pear-shaped to fit more comfortably around an infant's lips without interfering with the infant's nose. When nipple 20 is accepted by the mouth of an infant, the first surface 32 of guard 30 rests against the outer surfaces of the lips of the infant, as is the case with common styles of pacifiers. The rear of guard 30, opposite first surface 32, includes a male connector 34 configured to secure mouthpiece portion 50 to cleaning component 40. The female connector 44 of cleaning component 40 receives the male connector 34 of guard 30 to releasably join mouthpiece portion. In a preferred embodiment (as shown in FIG. 1), male and female connector 34 and 44 are threaded and form a double thread when joined, and the threading results in a watertight join.

Figure 2:
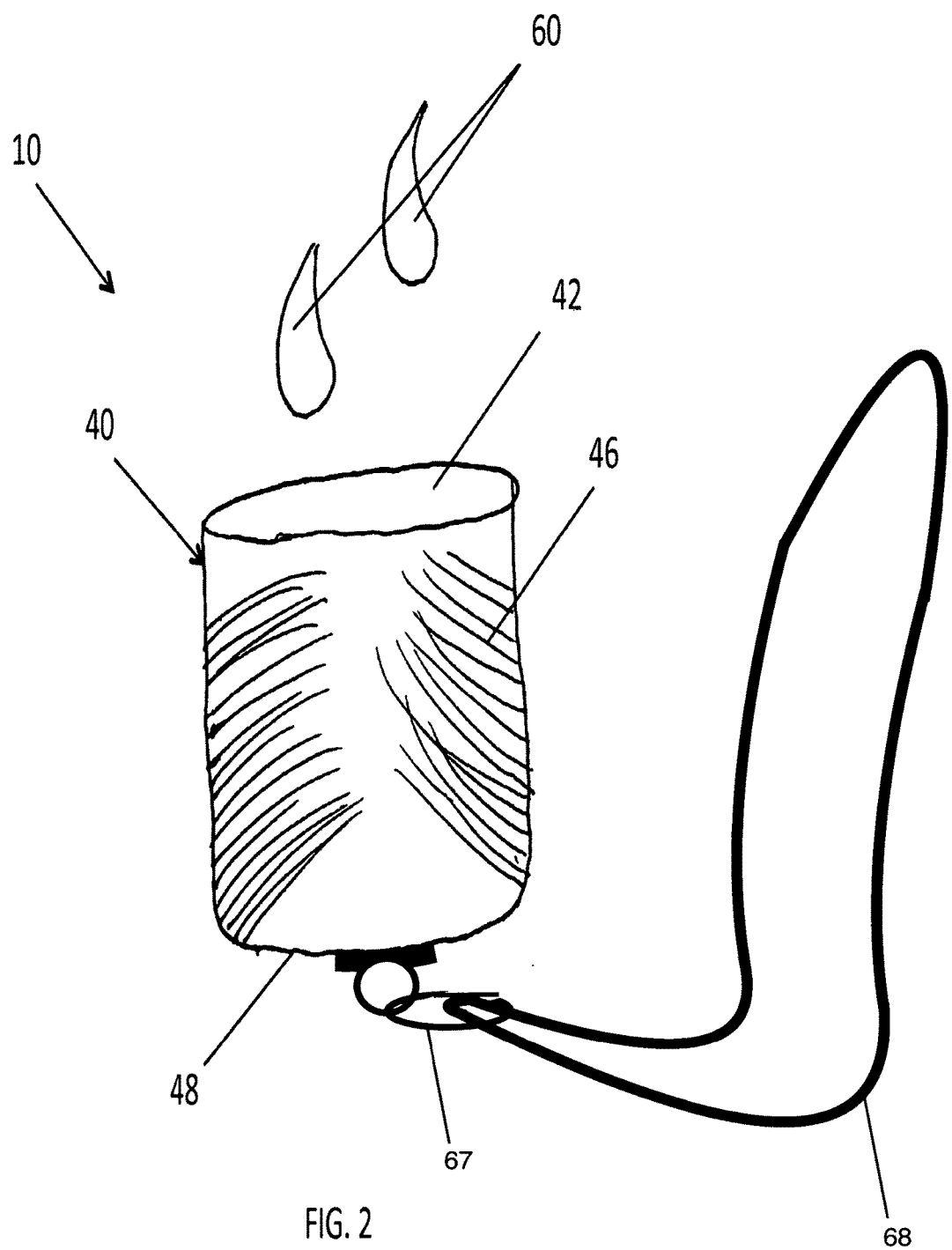
FIG. 2 shows a side elevation cut-away view of the cleaning portion of the pacifier, according to an embodiment of the present invention.

FIG. 2 shows an embodiment of the cleaning component 40 of pacifier 10. Cleaning component 40 has a generally cylindrical body with an enclosed end 48 and an opening 42 at the opposing end. In one embodiment, the female connector (not shown) of cleaning component 40 can be a thread protruding from the inside surface of cleaning component 40 near opening 42 (as depicted in FIG. 1). Bristles 46 are attached to the inside of cleaning component 40 to facilitate the removal of debris and germs when nipple 20 is inserted into cleaning component 40. In a preferred embodiment, bristles 46 line the entire interior of cleaning component 40. In one embodiment the bristles 46 are angled towards the opening 42, and in another they are angled towards the enclosed end 48. A child-safe sanitizing solution 60, such as lemon juice, may be added onto bristles 46 and inside cleaning component 40 to sanitize nipple 20.

Figure 3:
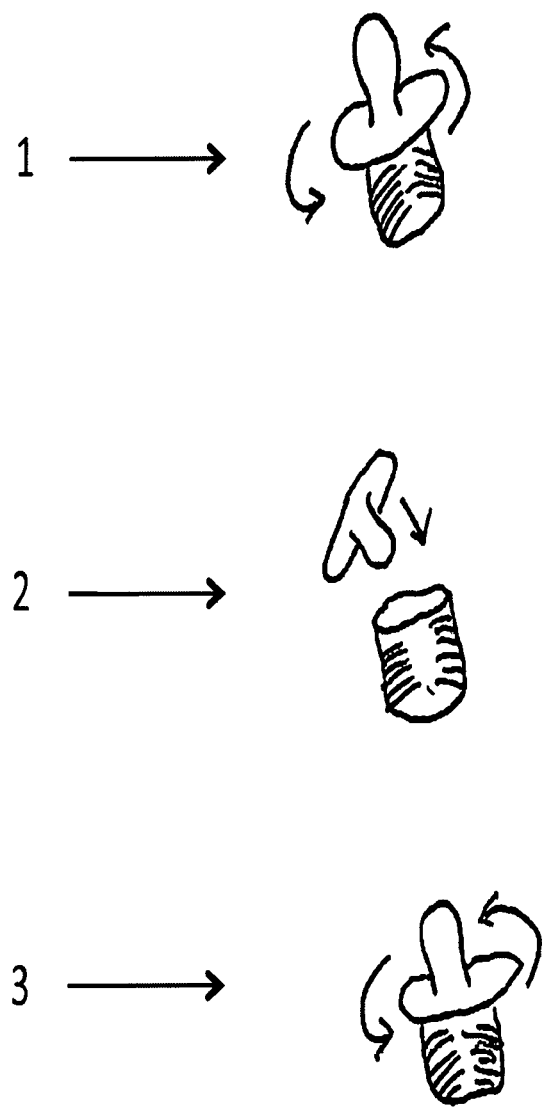
FIG. 3 shows a visual depiction of the method of cleaning the nipple using the pacifier, according to an embodiment of the present invention.

FIG. 3 shows a method of using pacifier 10 comprising steps 1 through 3. In step 1, assuming cleaning component 40 is connected to mouthpiece portion 50, the user separates the cleaning component from mouthpiece portion 50. In one embodiment, the male and female connectors, 34 and 44 respectively, are interconnecting threads and therefore, mouthpiece portion 50 can be separated from cleaning component 40 by unscrewing or twisting cleaning component 40 apart from mouthpiece portion 50. In step 2, the user flips mouthpiece portion 50 around so that nipple 20 can be dipped or inserted into cleaning component 40 through opening 42. The user can then clean and scrub nipple 20 by moving nipple 20 around inside of cleaning component 40. Finally, in step 3, user removes nipple 20 from the inside of cleaning component 40, flips mouthpiece portion 50 back around so that male connector 34 can be inserted into opening 42 and female connector 44 of cleaning component 40, thereby resealing or closing cleaning component 40. Therefore, mouthpiece portion 50 essentially acts as a lid for cleaning component 40, capable of being twisted on or off by the use of a double thread (i.e., the male and female connectors) in a preferred embodiment.

In an embodiment, a tether 69 can be connected to the outside to cleaning component 40 in order to more easily carry or hold onto pacifier 10. In a preferred embodiment, the strap or tether would be positioned on the enclosed end 48 of cleaning component 40 (see FIG. 2). In an embodiment, the strap is a connection 67 capable of being attached to a clothing accessory. In one embodiment, a strap 68 can be a lanyard to be worn around the users neck or attached to a clothing accessory, such as a backpack or purse. In an embodiment, the tether 69 can be connected to guard 30 and cleaning component 40 to keep the two parts connected so that one part is not easily dropped or lost.

In an embodiment, nipple 20 is an orthodontic nipple designed to help support the natural shape of the palate of the infant and can take a bulbous shape. In an embodiment, nipple 20 is made of a flexible material including, but not limited to, silicone, rubber, latex, plastic, or any combinations thereof.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

I claim:

1. A pacifier consisting of:
   a. a guard, having a first surface and an opposite facing second surface, the second surface having a threaded connector disposed on the second surface;
   b. a nipple attached to and outwardly extending from the first surface of the guard;
   c. a detachable cleaning component having a threaded opening to receive the threaded connector, and having a single, generally cylindrical body, the detachable cleaning component consisting of:
      i. one or more sidewalls having the threaded opening contained therein at one end of the one or more sidewalls;
      ii. a base opposite the threaded opening, wherein the one or more sidewalls separate the base and the threaded opening, and wherein the threaded opening is wider than the nipple of the first surface;
      iii. a plurality of bristles attached to an interior surface of the one or more sidewalls;
      iv. and wherein the guard of the pacifier extends radially beyond the cleaning component, when the cleaning component is threadably engaged with the threaded connector;
   wherein the plurality of bristles are contained entirely within the cleaning component, wherein the plurality of bristles are configured to remove contaminates from the nipple, wherein the cleaning component is capable of sanitizing the nipple by providing a sanitizing solution therein, and wherein the threaded opening sealingly connects the guard to the cleaning component.

2. The pacifier of claim 1, wherein the nipple is elongated in shape with a bulbous end portion extending away from the guard.

3. The pacifier of claim 2, wherein the nipple is a flexible material selected from the group consisting of plastic, silicon, latex, rubber, or a combination thereof.

4. The pacifier of claim 3, wherein the guard is curved to comfortably fit over an infant's lips.

5. The pacifier of claim 1, wherein the plurality of bristles are inclined towards the opening of the cleaning component.

* * * * *